(12) United States Patent
Rostaing

(10) Patent No.: US 8,372,491 B2
(45) Date of Patent: Feb. 12, 2013

(54) METHOD FOR COLD PLASMA TREATMENT OF PLASTIC BOTTLES AND DEVICE FOR IMPLEMENTING SAME

(75) Inventor: Jean-Christophe Rostaing, Versailles (FR)

(73) Assignee: L'Air Liquide Societe Anonyme pour l'Etude et l'Exploitations des Procedes Georges Claude, Paris (FR)

( * ) Notice: Subject to any disclaimer, the term of this patent is extended or adjusted under 35 U.S.C. 154(b) by 849 days.

(21) Appl. No.: 12/375,789

(22) PCT Filed: Jul. 26, 2007

(86) PCT No.: PCT/FR2007/051728
§ 371 (c)(1),
(2), (4) Date: Jul. 30, 2009

(87) PCT Pub. No.: WO2008/015358
PCT Pub. Date: Feb. 7, 2008

(65) Prior Publication Data
US 2009/0304950 A1 Dec. 10, 2009

(30) Foreign Application Priority Data
Aug. 1, 2006 (EP) .................................... 06300850

(51) Int. Cl.
*H05H 1/02* (2006.01)
*H05H 1/24* (2006.01)
(52) U.S. Cl. ........................................ 427/570; 427/569
(58) Field of Classification Search .................. 427/569, 427/570
See application file for complete search history.

(56) References Cited

U.S. PATENT DOCUMENTS

| | | | |
|---|---|---|---|
| 5,690,745 A | 11/1997 | Grunwald et al. | |
| 5,904,866 A | 5/1999 | Kasper | |
| 6,171,450 B1 | 1/2001 | Behnisch et al. | |
| 6,180,191 B1 | 1/2001 | Felts | |
| 6,328,805 B1 | 12/2001 | Rius | |
| 6,627,163 B1 | 9/2003 | Awakowicz et al. | |
| 6,919,114 B1 * | 7/2005 | Darras et al. ................ | 428/36.7 |
| 2004/0245667 A1 | 12/2004 | Behle et al. | |
| 2005/0019209 A1 | 1/2005 | Burger et al. | |

(Continued)

FOREIGN PATENT DOCUMENTS
EP    1 126 504    8/2001
WO    WO 03/014412    2/2003

(Continued)

OTHER PUBLICATIONS
International Search Report for PCT/FR2007/051728.

(Continued)

*Primary Examiner* — Kelly M Gambetta
(74) *Attorney, Agent, or Firm* — Christopher J. Cronin

(57) ABSTRACT

The present invention relates to a method for treating plastic bottles comprising an operation for cold plasma sterilization with non-germicidal gasses and/or an operation for the cold plasma deposition of a diffusion barrier layer, said method being characterized in that said cold plasma delivers adjustable nonthermal energy to the entire inside surface of the bottle, said cold plasma being generated either through a distributed propagation of microwaves having a maximum intensity in the vicinity of said surface or by a hollow cathode system adapted to the bottle and supplied with pulsed DC and/or RF voltage. The invention also relates to the devices for implementing the method.

16 Claims, 2 Drawing Sheets

U.S. PATENT DOCUMENTS

2005/0233077 A1* 10/2005 Lizenberg et al. .......... 427/248.1
2005/0269199 A1   12/2005 Pollak et al.
2008/0032059 A1*  2/2008 Zimmerer et al. ............ 427/458

FOREIGN PATENT DOCUMENTS

WO    WO 2006/010509    2/2006
WO    WO 2006/044254    4/2006

OTHER PUBLICATIONS

Tendero, et al, "Atmospheric Pressure Plasmas: A Review," Spectrochimica ACTA. Part B: Atomic Spectroscopy, NY, NY, US, vo. 61, No. 1, Jan. 2006, pp. 2-30.
PCT/FR2007/051728 Written Opinion dated Jul. 9, 2008.
Moisan, et al., "Microwave-Excited Plasma," Elsevier, 1992, Chapter 5.

* cited by examiner

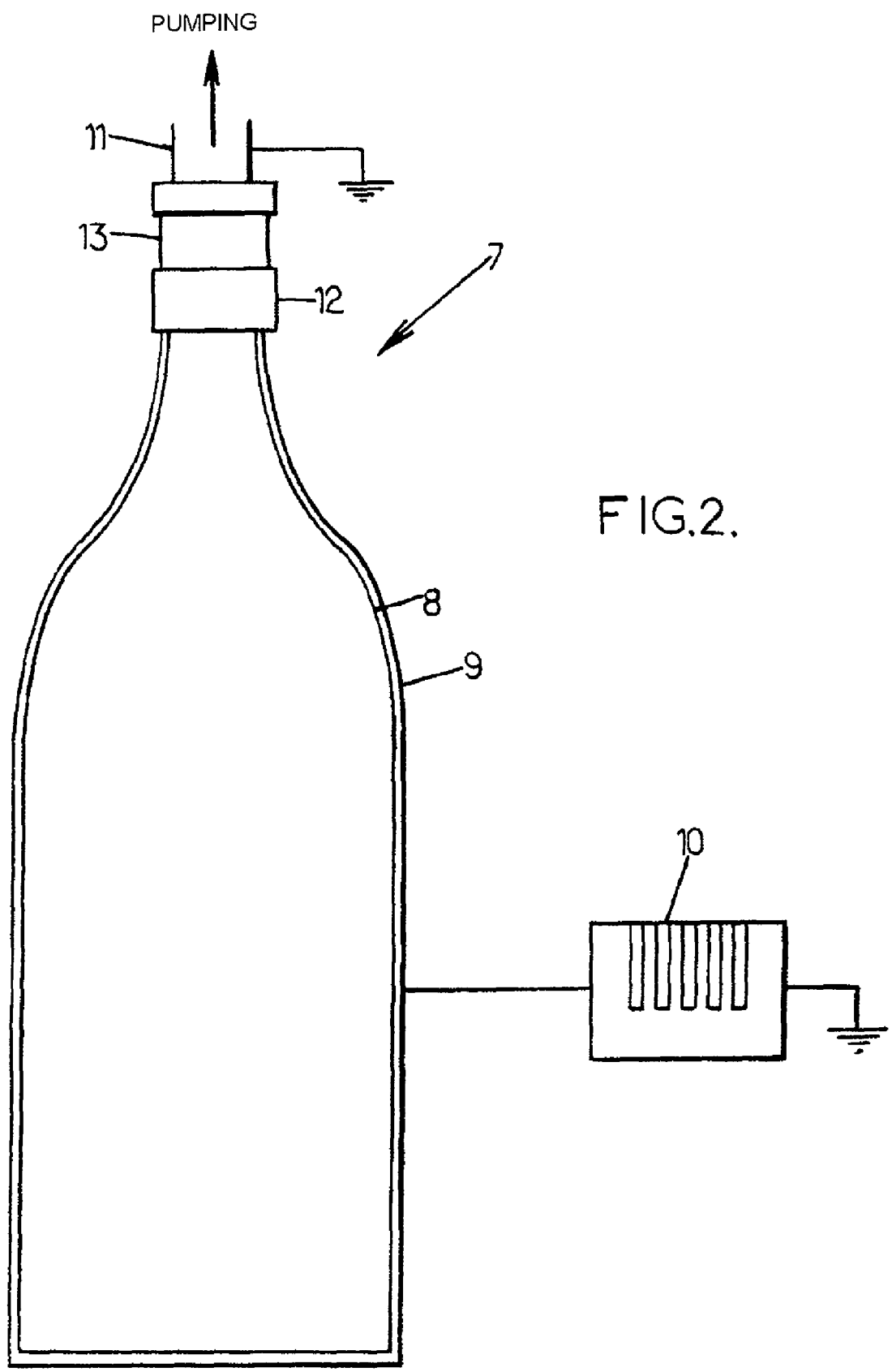

METHOD FOR COLD PLASMA TREATMENT OF PLASTIC BOTTLES AND DEVICE FOR IMPLEMENTING SAME

CROSS-REFERENCE TO RELATED APPLICATIONS

This application is a §371 of International PCT Application PCT/FR2007/051728, filed Jul. 26, 2007.

BACKGROUND

The invention relates to a method for continuously treating bottles by cold plasma, in particular plastic bottles for containing liquids, in particular food or pharmaceutical liquids. It also relates to devices for implementing this method.

In the context of the present invention, "cold" plasma means a plasma in which only the free electrons in the gas are raised to a high average energy level by the electrical excitation, while the molecules and atoms of the gas preserve an average thermal energy virtually corresponding to the ambient energy.

The sanitized packaging of liquids in plastic bottles is an expanding branch of the food packaging industry. It serves to lengthen the shelf life and/or to improve the microbiological safety. It is intended:

on the one hand, for mineral waters that are liable to contamination by pathogenic germs, and on the other hand, for longlife products sterilized at ultra-high temperature (UHT), to avoid reintroducing germs liable to make the products unfit for consumption (milk, soups, fruit juices).

Furthermore, for packaging some of these products, a need exists to increase the impermeability of the bottle in order to slow down the transfers of gaseous or volatile species to and from the exterior, in particular to prevent the loss of $CO_2$ in carbonated beverages and beer, the penetration of oxygen and/or the migration of flavors.

These sterilization and optionally impermeabilization operations must be integrated in the bottling line which extends from the molding of the bottles to the filling of said bottles.

Thus, the following operations are carried out in succession in a bottling unit:

molding of the bottles by extrusion blow molding;

optional production of a diffusion barrier, when the latter does not directly result from a multilayer including a barrier polymer;

sterilization of the finished bottle;

filling with the previously sanitized liquid;

and plugging after sterilization of the plug itself.

In this industry, boosting production and cutting costs are a crucial concern. The succession of abovementioned operations derives, for each, from a particular technology on a dedicated machine, and implies transfers between several stations of the production line. Attempts are therefore made to reduce the duration of each step, by adjusting or by changing the technology, and to minimize the number of transfers between various stations of the line.

Conventionally, on existing bottling lines, sterilization takes place by means of oxidizing chemical germicidal liquids, such as hydrogen peroxide, peracetic acid, ozonated water, etc. The bottle is dipped or internally sprayed, optionally heated, rinsed and dried before being filled. The method is effective, but it generates liquid effluents of which the cost of treatment is added to that of the process. Moreover, in general, the management of water circuits always incurs a risk of development of inadvertent or unavoidable microbial contamination, which the companies in the sector would like to eliminate.

For the other types of container for liquid food products, such as brick packs made from cardboard/aluminum/polymer multilayers, sterilization is carried out by ultraviolet radiation, particularly in pulsed mode, possibly associated with the application of an oxidizing germicidal liquid. In the case of the combination of ultraviolet radiation with a germicidal liquid, a synergistic effect is obtained and the sterilization may be very rapid. This method, which is ideal for treating the inside aluminum surfaces of these brick packs, is nevertheless too aggressive to be applied to bottles. Moreover, the use of UV lamps has the drawback that their radiation is directional, emitted in a clearly defined and limited solid angle. Before reaching the germs to be deactivated, it is therefore subject to shadow effects due to the geometry of the container treated. This method is therefore unsuitable for the bottle geometry.

It is known that electrical discharge plasmas maintained in certain gases at reduced pressure have a deactivating effect on microorganisms. Plasma sterilizations have been considered for food containers. Thus, document EP-1 068 032 considers the possibility of reducing the microbial contamination on the inside wall of the bottle by means of an oxygen microwave plasma excited in situ (without other details). However, it is stated that the efficiency is inadequate to do without a combination with a liquid stage in a second step. No plasma action mechanism is described.

As to the impermeabilization of the bottles, various solutions are proposed.

In the present application and according to the present invention, equal use is made of the terms "impermeabilization" or "deposition of a diffusion barrier layer" to designate the operation consisting in depositing, on a surface of the bottle, a layer for limiting the diffusion of gaseous molecules from outside the bottle to the interior thereof, and from inside the bottle to the exterior thereof.

Solutions based on a multilayer coextrusion incur risks of delamination, and are costly. Resin coatings are ineffective and raise recycling problems. In both cases, the polymer barrier remains in contact with the liquid and may interact with it, thereby causing transfers of chemical contaminants.

Another solution consists in producing barrier material layers on the polymer surface of the bottles by reaction with a chemical vapor excited by a plasma (method called plasma-enhanced chemical vapor deposition or PECVD). The principles of this technique are described below.

Firstly, the electromagnetic excitation energy, which may be continuous, optionally pulsed, or alternating in a frequency range possibly extending to microwaves, is absorbed in the gas to maintain a plasma state therein.

More precisely, the electric field strongly accelerates the free electrons present in the plasma. During their very rapid movement in the electric field, the electrons constantly undergo very frequent elastic collisions with the gas molecules.

Thus, they assume a statistical kinetic energy distribution similar to the conventional thermal agitation of the particles of a gas, but forced by the electrical excitation. The average kinetic energy acquired by the electrons by this mechanism is extremely high. It could be equivalent to a temperature for the electrons (thus by treating the average energy as kT, where k is the Boltzmann constant and T the absolute temperature in kelvin) of about several tens of thousands of kelvin.

However, the molecules and atoms of the initial gas do not directly receive the energy from the electric field and therefore preserve their statistical motion of natural thermal agitation. If the gas is initially cold, it remains so even when excited to pass into the plasma state. This is therefore referred to as "cold plasma". This particular state of a gas medium is generally engendered under reduced pressure. If the pressure is too close to atmospheric pressure, the elastic collisions of the electrons with the heavy gas particles, atoms and molecules, become so frequent that these particles themselves ultimately receive a high energy via said elastic collisions and their temperature may rise considerably. The plasma then deviates from the state that is advantageous for PECVD.

In the cold plasma, a large number of electrons have sufficient energy to cause inelastic collisions with the gas molecules, with the effect of an excitation, an ionization or a dissociation.

Ionization corresponds to the stripping of an electron from an atom or a molecule to create an electron-ion pair. This continuous production of new charged particles compensates for the losses of such particles by recombination in the volume or at the wall, and serves to maintain the plasma in steady state condition.

Dissociation of the initial gas molecules produces smaller fragments, atoms and radicals, comprising pending open chemical bonds which make these gas species extremely reactive, either with a solid surface, or with each other in the gas phase. In particular, the radicals formed from chemical molecules initially introduced into the gas, will be capable of reacting with the substrate surface to culminate in the incorporation of all or part of their constituent atoms in the lattice of a solid material of which a thin layer will thus grow progressively on the substrate surface. The reactivity of the radicals with the surface is so high that this incorporation and growth process does not require the surface to be raised to a temperature above ambient temperature to activate the reactions.

The excitation of the gas species, conferred by the inelastic electron collisions, is equivalent to raising these species to one of their energy levels quantified as electronic or vibrational, higher than the fundamental level. The order of magnitude of these energies is several electron-volts. To obtain such levels by a hypothetical heating of a gas, the temperature of this gas should therefore be several tens of thousands of kelvin or more. In a cold plasma, only a small fraction of the total number of heavy particles are raised to such energy levels, while the others remain close to their fundamental state, corresponding to ambient temperature.

This is referred to as nonthermal energy excitations. This energy carried by certain molecules, atoms, radicals or ions of the plasma can then be liberated at the level of the substrate surface when said species reach it. Its main advantage will be to assist the migration and rearrangement of the atoms during their incorporation in the material of the solid film. This makes it possible to deposit a high grade material, that is having good connectivity and a minimum of vacancies in the atomic lattice, and free of granular or columnar microstructures; this occurs without necessarily having to heat the substrate to a temperature significantly higher than ambient temperature, for example of 200 to 400° C., which is known to improve the quality but cannot be applied in the case of a polymeric substrate.

Another form of nonthermal energy which can be conveyed to the surface of a substrate in contact with a cold plasma, is that originating from the impact of ions accelerated by a deliberately applied potential difference between the plasma and the substrate, in a manner known per se.

A PECVD process for depositing barrier films on polymer models for food liquids must, in addition to an appropriate quality of the material, serve to guarantee a high deposition rate so that the technique is compatible with the production rates in this industry, and economically viable. A deposition rate of about 100 to 1000 nm/minute is generally suitable for depositing a layer having a thickness of a few tens to one hundred nm.

A high deposition rate implies the creation of a high concentration of precursor radicals capable of effectively condensing and reacting on the solid surface of the substrate and participating in the growth of the barrier layer. For this purpose, it is in particular necessary for the electron density of the plasma to be high, so that a sufficient number of electrons having the requisite energy are available to cause the inelastic collisions culminating in the formation of such precursor radicals.

To simultaneously maintain the quality of the layer material, it is clear that the input of nonthermal energy by excited species must be proportional to the average flux of atoms condensing on the surface to form the solid film. In fact, the higher the number of atoms incorporated per unit of time, the denser and also higher the nonthermal energy flux required to rearrange them by forming a regular atomic lattice.

The minimum nonthermal energy flux that may be required for deposition on the surface of the growing film to obtain good quality, depends on the material considered and on the chemistry of the gas phase. Moreover, this flux is also related to the pressure of the processed gas. The higher the pressure, the more the radicals tend to react prematurely in the gas phase before being individually positioned on the substrate surface. The reactions between radicals in the homogenous gas phase culminate in the formation of bonded atom clusters of larger size. When such an atom cluster reaches the surface, it tends to be incorporated while preserving its pre-existing atomic arrangement, by establishing bonds with the matrix and with neighboring clusters. This produces a less uniform and denser structure than that which would correspond to an optimal individual arrangement of each of the atoms in the lattice of the material constituting the thin film. To avoid this, added nonthermal energy must be available to dissociate the clusters reaching the surface so that the component atoms can then enter into an optimal lattice arrangement.

In practice, the various steps of the PECVD process described above (or more generally any cold plasma surface treatment process, in particular a sterilization treatment), must also be carried out by controlling the spatial distribution of the mechanisms. This is because the objects to be treated generally have a non-negligible size and the result of the treatment must be uniform throughout the surface of the substrate concerned. The effects of the treatment must not be exacerbated at certain locations, with potential damage to the substrate, and insufficient or non-existent elsewhere. For example, a deposited thin layer thickness must not vary by more than a few percent between any two points of the surface of a part to be coated, with a material quality that remains substantially the same everywhere.

In fact, the active species involved for example in a PECVD process, depositing radicals and particles carrying nonthermal excitation, correspond to transient states and have a short lifetime. More precisely, their mean path in the gas phase between their creation and their deexcitation and/or recombination (after which they have lost their advantageous properties for the method) have the same order of magnitude as the characteristic dimensions of a bottle. The plasma zone where the active species are created following the inelastic electron collisions must therefore be spread and fairly closely match the shape of the bottle surface. Moreover, the absorption of the electromagnetic power to maintain the plasma and to promote the inelastic electron collisions producing the active species, must be relatively uniform in this distributed plasma zone. In this way, the plasma treatment can be sufficiently rapid and complete.

However, it is a complex technical problem to supply electromagnetic power and to make it absorbed substantially uniformly to maintain the plasma in an arbitrary region of the space distributed in the vicinity of the object to be treated. This is because the power transfer is governed by the laws of electromagnetism, and also in a medium that is highly absorbent by definition. In particular, if one attempts to propagate progressive waves, they are rapidly damped due to the absorption along their propagation direction, hence a natural nonuniformity of the plasma thereby created.

It is not sufficient to control the plasma distribution to obtain a uniform treatment. The active species created must be effectively transportable to the surface, along a similar path (in the sense of its length and of the ambience crossed) for all of them. This transport is governed by the diffusion and dynamic conditions of the gas stream in the treatment device. For example, it is possible for a nonhomogenous boundary layer to be formed in the vicinity of the substrate surface by radical depletion. In fact, the resistivity of these radicals is very high, so that their consumption at the surface is much faster than their transport in the gas phase. The limitation of the deposition rate by transport in the gas phase generally leads to a nonuniform distribution imposed by the dynamic of the gas stream when a gas flow is maintained to continuously replenish the vapor of the chemical precursor consumed, as is generally the case in an industrial PECVD process.

All these problems are aggravated in the case of a bottle for beverages, which is an object having an awkward shape, having a high degree of geometric symmetry and a substantial extension (capacity up to 2 liters), whereas in the usual industrial cases, PECVD is applied to planar substrates of circular or rectangular shape. This requires the solution of highly complex problems of engineering of the plasma production device and of the deposition reactor.

Some authors (see for example documents U.S. Pat. Nos. 6,627,163, 5,904,866, US2005/0019209) have nonetheless come to a standstill on these aspects.

The technical solutions really available today for producing barriers on plastic bottles by PECVD have been forced to integrate specific technical options to contend with the abovementioned difficulties.

Thus SIDEL (commercial process known by the name "ACTIS") uses a microwave plasma excitation. The problem of the distribution and distributed absorption of the microwaves was circumvented, so to speak, by placing the entire bottle in a resonant cavity supplied at the frequency of 2.45 GHz. The bottle is placed in a dielectric chamber having a slightly larger diameter, itself placed in the conductive structure of the resonant cavity. The deposition method requires a vacuum of about 0.1 mbar in the bottle, implying a pumping installation of sufficient size. The chamber surrounding the bottle is also pumped, but to a lower vacuum, to avoid the contraction and crushing of the bottle, and also to prevent the undesirable ignition of a second plasma at the exterior.

Moreover, the deposition is carried out in static conditions, that is, the gas mixture comprising the chemical precursor is previously introduced under the pressure specified in the bottle, which is then isolated from the exterior. The plasma is then established to dissociate the chemical precursor vapor and to deposit the barrier layer. Due to the surface consumption of the precursor, a concentration gradient of active species between the gas phase and the surface is established. However, in static conditions, this gradient is the same at every point of the surface. Moreover, since the layer is very thin and the deposition step is short, the chemical precursor is not generally consumed in a high proportion and the average concentration in the gas phase does not decrease sharply inside the bottle over the deposition time.

The resonant cavity excitation mode nevertheless has certain drawbacks.

In a resonant cavity, only a series of discreet electromagnetic field distribution modes can exist, modes specific to the geometry of the cavity and therefore fixed once and for all. These eigenmodes of the cavity each correspond to a given distribution of the microwave field intensity in the cavity, and hence the distribution of the plasma density which is maintained by absorption of the energy of this microwave field. The inventors have found that in a cavity having a certain size, an eigenmode can be maintained in which the microwave field intensity distribution does not vary too much axially within a volume in which a bottle having a capacity of 600 ml may be enclosed. On the other hand, for higher cavity sizes, no such mode exists for which the field is sufficiently uniform axially to treat bottles having a larger capacity. In particular, commercial bottles having a capacity of 1.0 to 2.0 liters cannot be treated by this technique.

Another drawback of the "SIDEL ACTIS" microwave plasma device, which is also inherent in the excitation by resonant cavity, resides in the slight possibilities offered by the deposition of a controlled nonthermal energy on the inside surface of the bottle to promote the quality of the deposit. In fact, the microwave field does not have a pronounced maximum intensity in the vicinity of the bottle surface. In consequence, the creation of high internal nonthermal energy species under the effect of the inelastic electron collisions is not particularly promoted in this zone.

Nor is it possible, in this arrangement, to magnify and control the bombardment of the inside surface of the bottle by the plasma ions. The bottle is made from a dielectric material and there is no obvious means of charging it negatively in a distributable and adjustable manner. For example, it is not possible to apply a radiofrequency bias uniformly to this surface by means of a conductive electrode surrounding the bottle, because in this case, the microwaves can no longer pass through the wall of the bottle to maintain a plasma inside it.

Another solution could be to inject fast electrons produced by an electron gun toward the surface, as proposed by certain authors, but this alternative is neither simple nor inexpensive, and its practicability inside the bottle remains hypothetical.

This inadequacy in terms of nonthermal energy input on the bottle surface limits the choice of barrier materials of acceptable quality which can be deposited by this technique. It must in fact be limited to the deposit precursor chemistries which are known to be capable of providing a material of sufficient quality even under these conditions. This is the case for the deposition of hydrogenated amorphous carbon from the monomer acetylene. The latter has the drawback of a pronounced yellow color which makes it incompatible with certain applications such as containers for drinking water. It is also possible to deposit from organosilicate precursors layers still having a pronounced organic character. On the other hand, there is no commercial method based on this concept that would serve to deposit layers of inorganic silicon alloys of the type $SiO_xN_yC_zH_t$ which could be useful for optimizing the functionalities of barrier coatings.

Another solution is proposed by SIG Corpoplast with its "Plasmax" process. In this process, the device for applying microwaves to create a plasma in contact and close to the bottle surface, consists of a conductive chamber relatively closely surrounding the bottle, inside which the microwaves are injected by an antenna supplied with power via a waveguide. This structure is not a resonant cavity and does not have the geometry thereof. It is rather a hybrid structure from the electromagnetic standpoint, partially propagated and partially stationary. The microwave field can be expected to have wide inhomogeneities in the dimensions of the structure, with, on the one hand, standing wave intensity nodes and antinodes, and on the other hand, a rapid average axial decrease of intensity due to the property of propagating in an absorbent medium.

To succeed despite this in producing a relatively homogenous deposit on the whole inside surface of the bottle, the operating conditions are such that the deposition rate is not limited by the intensity of the plasma. More precisely, the injected microwave power is selected to be sufficiently high so that, at any point of the surface, the process of creating depositing radicals by dissociation of the precursor molecules reaches its saturation value with regard to the power. Thus, the deposition rate is imposed at every point by the precursor concentration and not by the microwave field intensity.

However, these conditions cannot be used continuously because due to the deliberately high intensity of the microwave field and of the plasma, the bottle material would rapidly suffer serious damage. To avoid this, a pulsed microwave power supply is used, the pulse duration and the repetition rate being adjusted so that the excess energy deposited, by finally being converted to heat, can be removed between two pulses.

The pulse power supply also serves, in a manner per se, to improve the uniformity of deposition because the gas phase in the vicinity of the bottle surface, depleted of active radicals during a deposition pulse, can be re-enriched between two consecutive pulses.

On the other hand, the control of the deposited nonthermal energy is highly imperfect in this arrangement. In fact, if the flow of depositing radicals is relatively uniform under these conditions, the same cannot be said of the nonthermal energy, which follows the spatial variations in intensity of the microwave field and of the plasma. In the development of the method, the pulse regime is adjusted so that no unacceptable damage can appear on the portions of the bottle surface which experience the lowest energy flux. This does not guarantee that the portions subject to the lowest energy are under optimal conditions for the compromise between radical flux and flux of excited nonthermal species, that is, deposition rates/layer quality. Thus it may be necessary to decrease the precursor concentration to lower the deposition rate. This limitation is undesirable because the potential users of this technology still demand a substantial increase in the treatment rate, which should typically rise from 10,000 to 50,000 bottles/hour.

In document WO2006010509 (KRONES) mention is made of such a combined treatment, but no details are provided for its implementation.

Thus a real need exists for a method for depositing impermeabilization layers while decreasing or eliminating the inadequacies of the current solutions, and/or a method for sterilizing, said method being intended to be integrated in a conventional bottling process, and not generating any aqueous effluents, not using germicidal chemical compounds, and implemented with a limited number of transfer steps.

SUMMARY OF THE INVENTION

The present invention serves to meet this need thanks to the impermeabilization achieved using a cold plasma maintained by means of devices different from those of the prior art, and thanks to its sterilization carried out exclusively by cold plasma using nongermicidal gases, the two steps being feasible in a single device. This device must serve to perform the sterilization and deposition of the barrier layer in a short time, compatible with the production rates demanded today by the industry.

In the present invention, the expression "nongermicidal gases" means gases which do not have germicidal activity under normal conditions, that is in the absence of plasma.

Thus the present invention relates to a method for treating bottles comprising an operation for cold plasma sterilization with nongermicidal gases and/or an operation for plasma enhanced chemical vapor deposition of a diffusion barrier layer, said method being characterized in that said high density plasma serves, on the one hand, to generate and deliver a high and spatially relatively uniform flux of radicals depositing on the inside surface of the bottle, and on the other hand, to provide an adjustable flux up to high levels of nonthermal energy in the form of ion bombardment or internal excitations of molecules, atoms, radicals or ions, and also relatively uniformly on said surface.

The invention also relates to a method for treating polymer bottles, in particular plastic bottles for containing liquids, in particular food or pharmaceutical liquids, comprising an operation for cold plasma sterilization with nongermicidal gases and/or an operation for plasma-enhanced chemical vapor deposition (PECVD) of a diffusion barrier layer, said method being characterized by the implementation of the following measures:

the cold plasma is generated, either by the distributed propagation of non-pulsed microwaves to the inside surface of the bottle, having a maximum intensity in the immediate vicinity of said surface, or by a hollow cathode system adapted to the bottle and supplied with pulsed DC or radiofrequency voltage;

the nonthermal energy flux on the inside surface of the bottle, in the form of ion bombardment or of deexcitation of internal electronic or vibrational levels of species of the plasma, is adjusted according to the flow of sterilizing species during the sterilization step, and according to the flow of free radical precursors of the solid material deposited during the barrier layer deposition operation.

The method may include one or more of the following aspects:

the sterilization and diffusion barrier layer deposition operations are carried out in one and the same device.

the cold plasma is generated by at least one surface wave microwave field applicator supplied by a microwave generator.

the cold plasma is generated by a plurality of surface wave applicators distributed and supplied by means of decor-related phases.

the microwaves are propagated in a distributed manner by means of microstrip applicators movably adjusted to the bottle.

the plasma used for the sterilization comprises gases selected from the group comprising $N_2$, $O_2$, $N_2O$, $H_2$, $H_2O$, Ar, He, Kr, X or mixtures thereof, preferably a $N_2/O_2$ mixture and even more preferably having a $N_2/O_2$ molar ratio of 95/5 to 80/20.

the sterilization time is 5 to 0.05 second, preferably 2 to 0.1 second and even more preferably 1 to 0.5 second.

the sterilization is carried out with a vacuum of 0.1 to 100 mbar.

the plasma used for the deposition of the diffusion barrier comprises gases selected from the group comprising monomers, gaseous carbon vectors, gaseous silicon compounds or mixtures thereof.

the diffusion barrier is deposited with a vacuum of 0.1 to 10 mbar.

the sterilization is carried out before the deposition of the diffusion barrier layer and that optionally, a finishing step is added to the cold plasma sterilization.

the diffusion barrier layer is deposited before the sterilization operation, the diffusion barrier layer optionally including protection against ultraviolet radiation.

The invention also relates to a device for generating a cold plasma of the surface-wave launcher type which has an annular shape and is suitable for being placed around a bottle to be treated, preferably at the median portion of the bottle, preferably slightly closer to the bottom of the bottle than to its neck, said device being supplied by a microwave generator.

The invention also relates to a cold plasma generating device of the hollow cathode type, the hollow cathode being adjusted to the shape of the bottle and the plasma being supplied by a pulsed DC negative bias and/or a radiofrequency bias.

The cold plasma generating device of the hollow cathode type may include one or more of the following aspects:

the hollow cathode consists of two half-shells.

the hollow cathode consists of an extrusion blow mold.

BRIEF DESCRIPTION OF THE FIGURES

FIG. 2 is a schematic of a hollow cathode device for cold plasma generation.

DETAILED DESCRIPTION OF THE INVENTION

Figure 1:
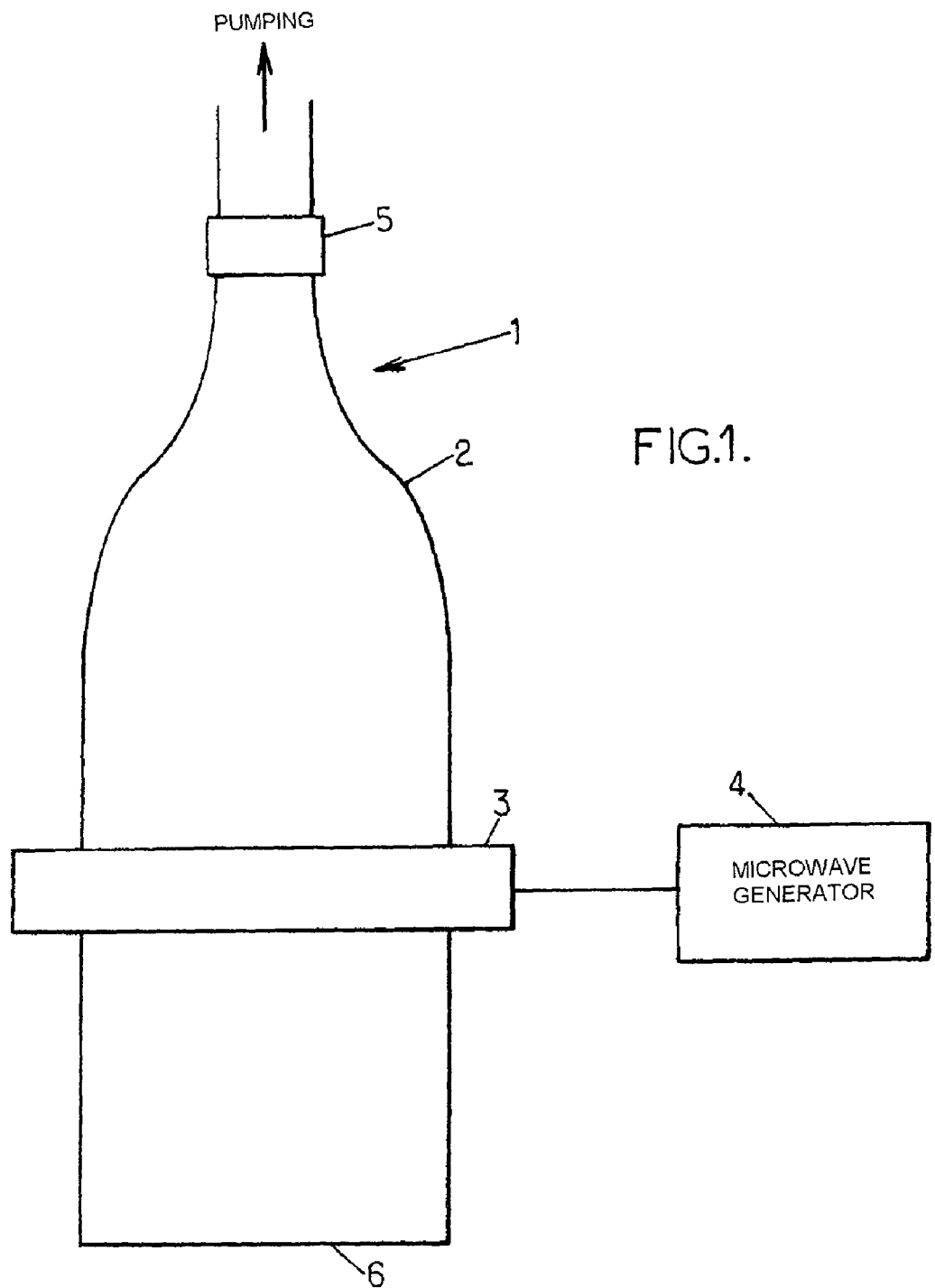
FIG. 1 is a schematic of a cold plasma generation device 1 of the surface-wave launcher type.

For a further understanding of the nature and objects for the present invention, reference should be made to the detailed description, taken in conjunction with the accompanying drawing, in which like elements are given the same or analogous reference numbers and wherein:

Preferably, the electron density of the plasma is between $10^9$ and $10^{12}$ cm$^{-3}$, more particularly between $10^{10}$ and $10^{11}$ cm$^{-3}$.

The nonthermal energy may be inherent in the species and due to the excitation of quantified electron and vibrational energy levels above the fundamental level, or is generated by the kinetic impact of the ions accelerated by a deliberately applied electric field bombarding the surface.

The plasma generated has a high and relatively uniform electron density over the whole inside surface of the bottle or in its immediate vicinity. In a plasma, the rate of creation of all the active species under the effect of inelastic electron collisions increases with the electron density. This is the case not only for the precursor radicals of PECVD deposition, but also for the excited UV emitting species and the oxidizing or reducing radicals involved in the plasma sterilization process. Furthermore, the deposition of nonthermal energy also serves to accelerate the process of microorganism deactivation, for example by assisting the chemical or physical erosion of the organic matter of the bacteria and viruses.

The plasma devices of the invention providing a high spatial uniform flux of depositing and sterilizing species on the inside surface of the bottle, and also a spatially controllable flux up to high values, spatially uniform, of nonthermal energy on the same surface, serve both to reduce the sterilization time and the time of deposition of the diffusion barrier.

According to the invention, the cold plasma is generated by a surface wave field applicator supplied by a microwave generator or by a hollow cathode system adapted to the bottle and supplied with pulsed DC voltage and/or radiofrequency voltage, the nonthermal energy deposit on the inside surface of the bottle being controlled up to a desired level, either by varying the incident microwave power, or by adjusting the self-bias DC voltage of the dielectric substrate consisting of the bottle with regard to the plasma.

According to a first embodiment, the plasma is generated by microwaves transmitted by a surface-wave field applicator also called surface-wave launcher.

This applicator is in the form of a conductive structure locally traversed by the dielectric chamber, consisting of the bottle, along which the surface wave is launched to maintain a plasma therein.

Such surface-wave launchers are known. A detailed description of the concept is given by M. Moisan and Z. Zakrzewski in chapter 5 of the work Microwave Excited Plasmas, Eds. M. Moisan and J. Pelletier, Elsevier, Amsterdam, 1992. By way of examples which can be used for the invention, mention can be made of the ro-box and the surfatron which are supplied with power from a coaxial line, and the surfaguide and surfatron-guide which are supplied with power by a hollow rectangular waveguide.

The choice of the surface-wave launcher depends on the type of property desired. Thus, the supply of microwaves by a waveguide serves to deliver high powers, but the coaxial line may assume the form of a flexible or semi-rigid cable, which may facilitate the installation of the device on the bottle at each treatment cycle for a high production rate.

One essential feature of the method for exciting a plasma by a surface wave is that the latter is supported by the plasma itself. The propagation of the surface wave is guided at the interface between the conductive plasma and the surface of the dielectric consisting of the bottle, thanks to this break in conductivity. The wave has its maximum intensity at this interface, that is, at the very surface of the bottle. Thus a maximum energy density is deposited in the plasma at this level (here on the inside), implying that the production rate of depositing free radical species and that of internal nonthermal energy carrier species, as well as the average energy of these species, are also a maximum at the bottle wall where the species are required to ensure a high deposition rate and good layer quality.

From the surface-wave launcher, the wave propagates along the dielectric wall parallel to the axis of symmetry of the bottle, being gradually damped as it gives up its power which is absorbed to maintain the plasma.

The wave extends to the point where there is no longer enough power for the plasma to exist and continue to support the propagation. When the microwave power is increased, the wave can propagate and maintain the plasma over a longer distance, and the plasma then extends increasingly further, thereby serving to adjust the scale of the treatment zone, without in any way altering the structure of the field applicator.

Surface-wave field applicators generally operate symmetrically, that is, two substantially identical waves can be launched on either side in opposite directions. The intensity of each wave, and consequently the density of the plasma, nevertheless progressively decrease (actually almost linearly) from the applicator, because of the absorption of the power with the continued propagation of the surface wave.

Thus, according to a particular embodiment, the surface-wave field applicator is placed in the median zone of the bottle, from which two opposite waves are propagated respectively toward the neck and toward the bottom. Due to the narrowing of the bottle neck, the wave is damped much slower during its propagation toward the neck than toward the bottom due to the narrower diameter (lower plasma volume to be maintained hence less power used). Accordingly, the applicator can be positioned nearer to the bottom than to the neck. The form assumed by the wave must also be verified when it matches the curvature of the bottle bottom, and in particular the power and/or distance from the applicator to the bottom must be adjusted so that no excessively pronounced interference is constructed, which is detrimental to the uniformity and control of the process. These adjustments constitute optimization operations for a person skilled in the art.

It is also possible to arrange more than one surface-wave applicator in order to compensate for the linear decreases in density of the plasma on either side of the isolated applicator and to produce an axial profile of the plasma density, hence of the deposition rate and of nonthermal energy, that is relatively constant. For this purpose, it is important to prevent the formation of standing waves by interference of opposite waves launched by two consecutive applicators. This can be obtained for example by supplying each of the applicators by a different generator, the phases of two waves emitted by two different generators being decorrelated so that the wave intensities are added and not the wave amplitudes.

The nonthermal energy flux toward the inside surface of the bottle depends on the incident microwave power. However, the flux of depositing radicals toward this surface may also depend via the electron density of the plasma, so that the two quantities are not independently adjustable. In actual fact, the practical cases of PECVD deposition correspond to a parametric domain in which the initial chemical precursor vapor is used at a high rate. Thus, it is still possible to adjust the flux of depositing radicals toward the surface by changing the concentration of precursor introduced into the bottle (or its partial pressure), relatively independently of the power.

The concept of a surface-wave field applicator is preferable to the others for maintaining the plasma under the conditions of the invention, because in this case, it is the plasma itself that constitutes the medium guiding the microwave propagation along the bottle wall. Hence there is no need for a local structure to apply the microwave power. However, it is perfectly conceivable to use a delocalized conductive structure to support the microwave propagation to distribute the microwaves in the vicinity of the bottle surface in order to maintain the plasma. For example, use can be made of microstrip lines adjusted to the shape of the bottle. These lines could advantageously be integrated in a flexible mobile structure movably adapting to the bottle to conduct the plasma treatment steps.

According to a second embodiment of the inventive method, the plasma is generated by a hollow cathode plasma device which, as in the case of excitation by microwaves, serves to maintain a plasma with a high electron density, that is highly effective for creating active species such as precursor radicals of solid material deposition.

The principle of the hollow cathode is completely different from that of the surface wave. At the intermediate frequencies between DC and radiofrequency voltage, a plasma is generally excited between two conductive electrodes connected to the poles of a generator (diode structure). At these frequencies, the rate of continuous creation of electron-ion pairs, by inelastic collisions of the charged particles already existing on the gas molecules, is much lower than with microwave (with AC voltage, the plasma density increases approximately with the square root of the frequency).

In the diode structure, there is no confinement of the charged species capable of increasing their lifetime by delaying their losses. In particular, the anode collects the electrons which are recombined and disappear on its surface, whether they are electrons created by inelastic collisions in volume, or those generated in the "gamma regime" following the bombardment of the cathode by energetic ions.

The arrangement called "hollow cathode" serves to preserve the energetic electrons in the plasma for a longer time, and to increase the ionization efficiency and the average density of charged species. The concept is based on a geometry in which the cathode determines a cavity with conductive walls, which surrounds the plasma in practically all directions, except for one or more small openings through which the field lines can return to an external anode.

A further beneficial effect may possibly be obtained on the plasma density, by adjusting the conditions in such a way that the mean free path of the electrons is slightly shorter than the diameter of the hollow cathode. The electrons repelled by the cathode do have a high probability of reaching the core of the plasma, and then in inducing inelastic collisions on the initially neutral molecules and thereby creating new electron-ion pairs, processes which finally further increase the charge density. The latter is typically higher by one order of magnitude with regard to a diode system, that is comparable to that which can be obtained in a microwave system.

The mean free path is mainly a function of the gas pressure, which must therefore be suitably selected according to the diameter of the hollow cathode.

According to a particularly advantageous embodiment, the hollow cathode is adjusted to the shape of the bottle which is placed inside and the plasma is permanently maintained by applying a pulsed negative DC bias, or a radiofrequency bias, or a combination of both.

On the contrary, since a bottle is made from a dielectric material, a permanent DC negative bias cannot be used. In fact, in this case, the inside surface collecting the positive ions of the plasma would acquire a positive charge that would progressively increase. The electric field created by this charge would oppose the external excitation field accelerating the electrons and, finally, cause the extinction of the plasma.

The diameter of the hollow cathode substantially corresponds in this arrangement to the diameter of the bottle. The latter is about 50 to 100 mm. To obtain a mean free path in this range and to take maximum advantage of the hollow cathode effect, the plasma maintenance pressure must be about 0.1 torr or less.

Advantageously, a replica of the extrusion mold or the extrusion mold itself can be used to produce the hollow cathode.

The external anode can be placed in the prolongation of the bottle neck, on the line serving for gas supply and pumping, with an intermediate electrical insulation. To avoid igniting the plasma in the space between the bottle and the hollow cathode, and also to prevent the deformation and crushing of the bottle, a lower vacuum is established in the bottle than in the space between the hollow cathode and the bottle.

When the space between the cathode and the mold imprint is very narrow, this space may even be kept under atmospheric pressure without the occurrence of the problems mentioned above.

The hollow cathode can be supplied with pulsed DC voltage with an amplitude, a pulse duration and an adjustable repetition rate. The choice of these parameters serves to control the density of the plasma with a certain degree of independence, and also the average value of the surface bias potential, hence the ion bombardment of the inside wall of the bottle. In this case, it is this ion bombardment that represents the nonthermal energy input on the inside surface of the bottle. The adjustment of the pulsed power supply normally is less advantageous here for improving the uniformity of deposition by attenuating the effect of depletion of the precursors of the gas phase (by allowing their replenishment between each cycle). In fact, the bottle does not represent an internal space with very narrow dimensions, and this depletion effect should not be important provided that the operation is conducted in steady state conditions, which is generally the case for PECVD inside the bottle.

As an alternative or in addition, the cathode may be biased by the application of a radiofrequency voltage. In this case, the self-bias effect exists in the same way as in a conventional diode electrode system. Since, in general, the electrons are more mobile in the plasma than the ions, the negative charge collected by the bottle wall in contact with the hollow cathode, during a positive alternation, is higher in absolute value than the positive charge collected during a negative alternation. The dielectric then acquires a negative permanent charge and a DC potential of the same sign, inducing a continuous ion bombardment of the inside surface of the bottle. Thanks to this self-bias, of which the amplitude is adjustable by adjusting the radiofrequency excitation parameters, it is possible to adjust with greater independence with regard to the other parameters, in particular those governing the deposition rate, the kinetic energy of the accelerated ions reaching the inside surface of the bottle, that is the nonthermal energy deposited on said surface. In the case of a radiofrequency excitation, the device comprises a radiofrequency shielding to the frame around the hollow cathode with air, or a solid dielectric, between the two conductors.

According to the invention, the sterilization and the deposition of the diffusion barrier layer are preferably carried out in the same plasma generating device. Obviously, according to the desired step, the plasma generation conditions and the gases employed are different.

Thus, the plasma used for sterilization comprises gases selected from the group comprising $N_2$, $O_2$, $N_2O$, $H_2$, $H_2O$ (water vapor), Ar, He, Kr, Xe or mixtures thereof.

Advantageously, use is made of a $N_2/O_2$ mixture. Preferably, the $N_2/O_2$ mixture is a mixture that is richer in oxygen than those used for medical sterilization, for example in a $N_2/O_2$ molar ratio of 95/5 to 80/20.

The bottle is thus placed under vacuum of about 0.1 to 10 mbar and the sterilization is carried out in a time as short as the time used in conventional methods of sterilization by the use of germicidal aqueous solutions. The duration of the sterilization step is 5 to 0.05 second, preferably 2 to 0.1 second and even more preferably 1 to 0.5 second.

A person skilled in the art is capable of adjusting the plasma conditions so that the plasma intensity is sufficient to sterilize without degrading structure of the polymer and the degeneration of the chemical species incompatible with food use or overheating of the polymer.

The mechanisms of microorganism deactivation by these plasmas are clearly explained and the active species involved are identified. The germs are killed by three types of mechanism: ultraviolet radiation emitted by the deexcitation of certain energy levels of molecules, ions and radicals, the oxidizing or reducing radicals reaching the genetic material after having diffused across the peripheral organic layers, and the physical or chemical erosion of the microorganism material resulting from the scattering of atoms by ion bombardment or deexcitation of internal electron or vibrational energy levels, or the chemical attack of the organic matter by oxidizing or reducing radicals, the latter also being facilitated by an input of nonthermal energy.

The plasma sterilization by the method described here, that is without using any chemical source product, but exclusively gases which only acquire their germicidal properties in the plasma because of the electromagnetic excitation, is a completely dry process but also an intrinsically clean process. In fact, the active species responsible for the deactivation of the germs, reducing and oxidizing radicals and various other excited species, have a transitory existence and disappear rapidly when the gas leaves the plasma zone, being deexcited and/or recombining to reform the species of the initial gas such as $O_2$ and $N_2$, plus possibly a low proportion of nitrogen oxides. The latter are easy to remove on an inexpensive device, for example a reactive adsorption system. The service life of the consumable and adsorbent is long owing to the low concentration of pollutants to be treated.

The sterilization step may be the subject of in-situ control by acquiring a physical parameter indicative of the species or species recognized as primarily responsible for the deactivation process. For example, an optical detector can track a characteristic signal of an identified oxidizing or reducing radical, or the UV intensity level in a certain spectral band, etc.

As to the step of deposition of a diffusion barrier, various precursor monomers are used as gases in the plasma, particularly carbon vectors such as hydrocarbons, or even silicon compounds according to the type of deposition considered.

In fact, the diffusion barrier layer may have any suitable composition, particularly an amorphous silicon alloy, such as a stoichiometric or nonstoichiometric oxide, a nitride, an oxynitride, etc., or a solid carbon compound, such as hydrogenated amorphous carbon in its various forms. The barrier layer may have a multilayer structure or a gradient of properties according to its thickness. For example, a more polymeric and organic layer can be deposited in the vicinity of the interface, to promote the adhesion and thermomechanical strength, and a denser, harder and inorganic layer on the outer surface. The substrate may be prepared before deposition for better adhesion, by any type of plasma pretreatment based on argon, nitrogen, oxygen, etc.

The adjustment according to the invention of the nonthermal energy flux in a manner proportional to the flux of depositing radicals serves to obtain a material of acceptable quality to constitute a barrier, while preserving a high deposition rate, for a wider range of compositions corresponding to different precursor chemistries. In particular, materials can be selected which do not have a residual color that restricts the range of their applications.

The controlled input of nonthermal energy can also be exploited to conduct the deposition method under a lower vacuum, for example of about 10 mbar, while preserving a high deposition quality despite the greater tendency to gas phase nucleation. This is only valid in the case of the surface-wave microwave system. For the whole of cathode system, the pressure increase rapidly causes the plasma density to leave the optimal conditions, and is highly disadvantageous to the treatment rate.

According to a particular embodiment, the inventive method comprises a first sterilization step followed by a second diffusion barrier deposition step and, optionally, a third sterilization "finishing" step.

This embodiment is particularly advantageous when the sterilization is conducted in "hard" plasma conditions allowing very rapid sterilization. Thus, even if these conditions lead to a slight alteration of the surface structure, the polymer material, after being coated with its inorganic barrier, should recover its food compatibility properties. Furthermore, the deposition plasma may itself contain sterilizing species, particularly in the case of a $SiO_x$ material requiring an oxidizing precursor gas, and the PECVD deposition is a bacteriologically "clean" method in principle.

An additional sterilization "finishing" step may be considered, even if it is not preferred due to the fact that it would be penalizing in terms of time.

According to another particular embodiment, the inventive method comprises a first step of PECVD deposition, optionally with the application of a UV treatment, and a second sterilization step.

In the case in which the sterilization is carried out after the deposition, the diffusion barrier, which is made from an inorganic material, is much more resistant to the action of the oxidizing plasma than the bare polymer. However, it is necessary to prevent the action of UV photons across the barrier layer, on the interface thereof with the polymer substrate. Experience shows that this may be a factor of decohesion following the splitting of chemical bonds at this interface. To eliminate this risk, all or part of the thickness of the deposit layer can, if necessary, be given UV barrier properties. For this purpose, it suffices, for example, to adjust the composition of a $SiO_x$ layer, in order to adjust the absorption threshold to the spectral boundary between the visible and UV. The absorption transition is not sudden but, even if a fraction of the blue/violet spectrum is absorbed, the thickness of the barrier is generally too low for a yellowish color to be perceptible.

The inventive method is integrated in the overall bottling process and is immediately conducted after the extrusion, optionally after cooling the bottle.

The cooling step is particularly necessary when the PECVD deposition is carried out before sterilization. In fact, even if the temperature promotes the deposition quality, after cooling, the differential thermal stresses between the polymeric substrate and the inorganic barrier layer may be excessive and cause a detachment of the layer.

The invention also relates to the cold-plasma generating devices for implementing the inventive method.

Thus, according to a first embodiment, the inventive device is an annular surface-wave launcher which is placed around the bottle to be treated. It is preferably placed at the median portion of the bottle, preferably slightly closer to the bottom of the bottle than to its neck. Such a device is shown in FIG. 1.

FIG. 1 schematically shows a cold plasma generation device 1 of the surface-wave launcher type. The model to be treated 2 is placed inside an annular applicator 3 supplied by a microwave generator 4. A pumping system (not shown) for adjusting the vacuum in the bottle, is placed at the neck 5 of the bottle 2.

When the system is in operation, the vacuum is produced in the bottle by the pumping device, which also serves to circulate the gas stream required under the requisite reduced pressure, either for the sterilization or for the deposition of the diffusion barrier. An appropriate rig, known to a person skilled in the art, serves to inject the suitable gas mixture into the bottle. The method may also be carried out in static conditions by introducing a fixed quantity of gas mixture. In fact, the relative consumption of the reactive components of the mixture is immaterial. The microwave generator is operated and the surface wave then propagates both from the annular applicator 3 toward the bottom 6 of the bottle and from the annular applicator 3 toward the neck 5.

According to a second embodiment, the cold plasma generation device is of the hollow cathode type, the hollow cathode being adjusted to the shape of the bottle and consisting of two half-shells allowing easy opening and closing, and the plasma being supplied by a pulsed negative DC bias and/or a radiofrequency bias.

FIG. 2 schematically shows a hollow cathode device for cold plasma generation.

In this device 7, the bottle 8 is placed inside a hollow cathode 9 consisting of two half-shells. Said hollow cathode 9 is adjusted to the shape of the bottle 8.

The hollow cathode 9 is supplied with pulsed negative DC voltage by a generator 10. The anode 11 is placed at the neck 12 of the bottle. The anode is connected to earth. The insulating element 13, placed at the neck, separates the anode from the cathode. As in the preceding case, a pumping system (not shown) is placed at the neck of the bottle, and also a device for injecting gases to maintain a composition, a reduced pressure and a given or zero flow of process gases.

The integration of the plasma devices with the existing infrastructures on the bottling line takes account, if applicable, of inherent stresses. For example, in the case of a hollow cathode device, since the cathode is raised to a highly negative potential with regard to earth, electrical insulations must therefore be produced with regard to the rest of the installation to work in complete reliability and safety. In the case in which the hollow cathode is supplied by radiofrequency, the RF shielding must be integrable while complying with the mechanical architecture of the rest of the machine.

The hollow cathode is made from two half-shells to permit loading and unloading of the bottle.

The device may comprise a double wall, the hollow cathode on the inside and an enveloping anode on the outside, with a dielectric between the two walls and means for providing good electrical continuity of each of the internal and external conductors, while maintaining good insulation between them, when the shell is closed.

In the case in which the hollow cathode consists of the mold itself, the mechanical connections of the mold to the frame must be provided with an insulating material, for example ceramic hinge parts.

The means for maintaining the vacuum, for rapidly opening and closing the treatment chamber, for injecting the process gases, for loading, unloading the bottles, and for handling said bottles, are those conventionally used in bottling lines.

The invention is described in greater detail in the examples that follow, which are provided for illustration exclusively.

EXAMPLE 1

The invention can be applied to any aseptic bottling line.

A polymer preform is transformed into a bottle in a conventional extrusion blow molding device. The just extruded bottles are conveyed to a treatment station comprising a plasma device as shown in FIG. 1.

The means for maintaining the vacuum, for rapidly opening and closing the treatment chamber, for injecting the process gases, for loading, unloading the bottles, and for handling said bottles, are those conventionally used in bottling lines.

A vacuum of 1.0 mbar is produced inside the bottle and an input of a $N_2/O_2$ mixture in a $N_2/O_2$ molar ratio of 90/10 is introduced into the bottle. A vacuum of 50 mbar around the outer wall of the bottle is created to prevent any deformation thereof.

EXAMPLE 2

A polymer preform is transformed into a bottle in a conventional extrusion blow molding device. The just extruded bottles are conveyed to a treatment station comprising a plasma device as shown in FIG. 2, in which a metal replica of the extrusion mold constitutes the hollow cathode.

The means for maintaining the vacuum, for rapidly opening and closing the treatment chamber, for injecting the process gases, for loading, unloading the bottles, and for handling said bottles, are those conventionally used in bottling lines.

A vacuum of 0.2 mbar is produced inside the bottle and an input of a $N_2/O_2$ mixture in a $N_2/O_2$ molar ratio of 90/10 is introduced into the bottle.

The level of sterilization of the bottle is monitored using an optical detector that tracks a characteristic signal of an identified oxidizing radical, for example atomic oxygen. If the level of this signal has remained satisfactory for a predefined time (about 1 second), the gas species are then removed and replaced by species required for preparing the diffusion barrier.

In a first step, the inside surface is pretreated to promote the adhesion by using an argon-based plasma; a diffusion barrier is then deposited by introducing a mixture of argon, oxygen and silane into the plasma.

When the thickness of the diffusion layer is sufficient, the vacuum is interrupted and the bottle is removed from the extrusion mold and then cooled before being conveyed to the filling station. Simultaneously, a new preform is introduced into the extrusion blow mold.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for treating a polymer bottle in the absence of contact with liquid effluents, wherein the polymer bottle has an inner surface and an outer surface, the method comprising cold plasma sterilization of the polymer bottle with a nongermicidal gas, wherein:
   the cold plasma is generated, either by distributed propagation of non-pulsed microwaves to the inner surface of the bottle or by a hollow cathode system, wherein the microwaves have a maximum intensity in the immediate vicinity of said inner surface, and wherein the hollow cathode system is adapted to the bottle and supplied with pulsed DC voltage or radiofrequency voltage;
   the nonthennal energy flux on the inner surface of the bottle, in the form of ion bombardment or of deexcitation of internal electronic or vibrational levels of species of the plasma, is adjusted according to a flow of sterilizing species during the sterilization step, the non-thermal energy being adjusted either by varying the incident microwave power, or by adjusting the self-bias DC voltage of the dielectric substrate consisting of the bottle with regard to the plasma;
   the cold plasma sterilization is conducted without oxidizing a germicidal component.

2. A method for treating a polymer bottle in the absence of contact with liquid effluents, wherein the polymer bottle has an inner surface and an outer surface, the method comprising the steps of
   (a) sterilizing the inner surface exclusively with cold plasma; and
   (b) depositing a barrier layer on the inner surface to create a sterilized polymer bottle having substantially reduced amounts of contaminants and a substantially reduced permeability to gases as compared to the untreated polymer bottle,
   wherein step (a) further comprises the steps of:
      exposing the inner surface of the polymer bottle to a nongermicidal gas; and
      creating a nonthermal energy flux within the bottle to energize the nongeimicidal gas under conditions operable to create the cold plasma using a cold plasma generation device such that the inner surface of the polymer bottle is sterilized;
   wherein step (b) further comprises the steps of:
      exposing the inner surface of the polymer bottle to a diffusion barrier gas; and
      depositing a diffusion barrier layer on the inner surface of the polymer bottle under conditions operable to promote plasma-enhanced chemical vapor deposition (PECVD);
   wherein the cold plasma generation device is selected from the group consisting of an annular surface-wave launcher and a hollow cathode system, the annular surface-wave launcher being operable to distribute propagated non-pulsed microwaves having maximum intensity proximate the inner surface, the hollow cathode system being adapted to the outer surface of the bottle, and the hollow cathode system being supplied with pulsed DC voltage or radiofrequency voltage.

3. The method of claim 2, wherein step (a) and step (b) are carried out in the same device.

4. The method of claim 2, wherein the cold plasma generation device is the annular surface-wave launcher, and the cold plasma is generated by at least one surface wave microwave field applicator supplied by a microwave generator.

5. The method of claim 4, wherein the cold plasma is generated by a plurality of surface wave applicators distributed and supplied by decorrelated phases.

6. The method of claim 4, wherein the microwaves are propagated in a distributed manner by microstrip applicators movably adjusted to the outer surface of the bottle.

7. The method of claim 2, wherein the nongermicidal gas is selected from the group consisting of $N_2$, $O_2$, $N_2O$, $H_2$, $H_2O$, Ar, He, Kr, Xe, and mixtures thereof.

8. The method of claim 2, wherein the nongermicidal gas consists essentially of $N_2$ and $O_2$.

9. The method of claim 2, wherein step (a) is conducted for a time of 0.05 to 5 seconds.

10. The method of claim 2, wherein step (a) further comprises the step of applying a vacuum to the bottle such that the pressure within the bottle is between 0.1 to 100 mbar.

11. The method of claim 2, wherein the diffusion barrier gas is selected from the group consisting of monomers, gaseous carbon vectors, gaseous silicon compounds, and mixtures thereof.

12. The method of claim 2, wherein step (b) further comprises the step of applying a vacuum to the bottle such the pressure within the bottle is between 0.1 to 10 Mbar.

13. The method of claim 2, wherein step (a) is carried out before step (b), and the method further comprises a second sterilizing step following step (b).

14. The method of claim 2, wherein step (b) is carried out before step (a), wherein step (b) further comprises the step of applying a UV protection layer to the barrier layer.

15. The method of claim 2, wherein the cold plasma generation device is the hollow cathode system, wherein the hollow cathode system comprises two half-shells that, when joined together, are adaptable to the outer surface of the bottle.

16. The method of claim 2, wherein step (a) and step (b) are conducted at ambient temperatures.

* * * * *